(12) United States Patent
Hirokawa et al.

(10) Patent No.: US 9,562,912 B2
(45) Date of Patent: Feb. 7, 2017

(54) METHOD OF IDENTIFYING ABNORMAL CELLS BY EXPRESSION LEVELS OF ETFB

(75) Inventors: Shigenari Hirokawa, Tokyo (JP); Hiroyuki Kitajima, Tokyo (JP); Tomomasa Shimanuki, Yokohama (JP)

(73) Assignee: POLA PHARMA INC., Tokyo (JP)

( * ) Notice: Subject to any disclaimer, the term of this patent is extended or adjusted under 35 U.S.C. 154(b) by 17 days.

(21) Appl. No.: 14/342,774

(22) PCT Filed: Dec. 27, 2011

(86) PCT No.: PCT/JP2011/080247
§ 371 (c)(1),
(2), (4) Date: Mar. 4, 2014

(87) PCT Pub. No.: WO2013/035209
PCT Pub. Date: Mar. 14, 2013

(65) Prior Publication Data
US 2014/0235491 A1  Aug. 21, 2014

(30) Foreign Application Priority Data
Sep. 5, 2011 (JP) ................................ 2011-206582

(51) Int. Cl.
| C12Q 1/68 | (2006.01) |
| G01N 33/68 | (2006.01) |
| G01N 33/50 | (2006.01) |
| C12N 15/113 | (2010.01) |

(52) U.S. Cl.
CPC ......... *G01N 33/6872* (2013.01); *C12N 15/113* (2013.01); *C12Q 1/6883* (2013.01); *G01N 33/5044* (2013.01); *G01N 33/6893* (2013.01); *C12Q 2600/158* (2013.01); *G01N 2800/20* (2013.01)

(58) Field of Classification Search
None
See application file for complete search history.

(56) References Cited

U.S. PATENT DOCUMENTS

| 2007/0014767 A1 | 1/2007 | Ezquerro Saenz et al. |
| 2008/0187918 A1 | 8/2008 | Kido et al. |
| 2010/0047261 A1 | 2/2010 | Hoerr et al. |
| 2010/0112583 A1 | 5/2010 | Ichiishi et al. |
| 2010/0137149 A1 | 6/2010 | Shin et al. |
| 2011/0229558 A1 | 9/2011 | Niitsu et al. |

FOREIGN PATENT DOCUMENTS

| JP | 2009-040796 A | 2/2009 |
| JP | 2010-059124 A | 3/2010 |
| JP | 2010-508014 A | 3/2010 |
| JP | 2010-107461 A | 5/2010 |
| JP | 2010-514441 A | 5/2010 |
| JP | 2010-222351 A | 10/2010 |
| WO | WO 2006/054722 A1 | 5/2006 |

OTHER PUBLICATIONS

Zhang et al., The Journal of Investigative Dermatology, 2003, vol. 120, pp. 849-857.*
Hirokawa et al., Journal of Dermatological SCience, 2011, vol. 64 pp. 119-126.*
Ishikawa et al., Int. J. Radiation Oncology Biol. Phys., 2006, vol. 65(1) pp. 234-245.*
McAnulty, IJBCB, 2007, vol. 39 pp. 666-671.*
Genbank ETFB, CR456827.1, dowloaded Jul. 27, 2015 from: http://www.ncbi.nlm.nih.gov/nuccore/48145770.*
Palmfeldt et al., Proteome Science, 2009, vol. 7, pp. 1-10.*
Moulin et al., Journal of Cellular Physiology, 2004, vol. 198 pp. 350-358.*
Extended European Search Report for European Patent Application No. 11872070.5, issued on Feb. 26, 2015.
Hinz, "Formation and Function of the Myofibroblast Tissue Repair," *Journal of Investigative Dermatology*, vol. 127, pp. 526-537 (2007).
Hirokawa et al., "Knockdown of electron transfer flavoprotein β subunit reduced TGF-β-induced α-SMA mRNA expression but not COL1A1 in fibroblast-populated three-dimensional collagen gel cultures," *Journal of Dermatological Science*, vol. 68, pp. 179-186 (2012).
"*Homo sapiens* full open reading frame cDNA clone RZPDo834G0315D for gene ETFB, electron-transfer-flavoprotein, beta polypeptide; complete cds, incl. stopcodon," Accession No. CR456827, CR456827.1, [online], National Center for Biotechnology Information, posted date Oct. 16, 2008, retrieval date Feb. 23, 2012, Internet, http://www.ncbi.nlm.nih.gov/nuccore/48145770.
Au et al., "When the Smad signaling pathway is impaired, fibroblasts advance open wound contraction," *Experimental Molecular Pathology*, vol. 89(3), pp. 236-240 (2010).
Grinnell et al., "Cell Motility and Mechanics in Three-Dimensional Collagen Matrices," Annual Review of Cell and Developmental Biology, vol. 26, pp. 335-361 (2010).
Hadjipanayi et al., "Close dependence of. fibroblast proliferation on collagen scaffold matrix stiffness," *Journal of Tissue Engineering and Regenerative Medicine*, vol. 3, pp. 77-84 (2009).
Henriques et al., "Mutational hotspots in electron transfer flavoprotein underlie defective folding and function in multiple acyl-CoA dehydrogenase deficiency," *Biochimica et Biophysica Acta*, vol. 1802, pp. 1070-1077 (2010).

(Continued)

*Primary Examiner* — Mindy G Brown
(74) *Attorney, Agent, or Firm* — Knobbe, Martens, Olson & Bear, LLP

(57) ABSTRACT

Provided is a method for identifying and suppressing abnormal growth of fibroblasts at an early stage. Provided is a method for identifying the growth state of fibroblasts using as an index the level of expression of ETFB (electron transfer flavoprotein beta subunit), comprising: judging, in cases where the level of expression of ETFB is high, that there is a high probability that fibroblasts are abnormally growing; and judging, in cases where the level of expression of ETFB is low, that there is a high probability that fibroblasts are normally growing. Further, by inhibition of ETFB, abnormal growth of fibroblasts can be suppressed.

7 Claims, 3 Drawing Sheets

(56) References Cited

OTHER PUBLICATIONS

Hirokawa et al., "Identification of ETFB as a candidate protein that participates in the mechanoregulation of fibroblast cell number in collagen gel culture," *Journal of Dermatological Science*, vol. 64, pp. 119-126 (2011).

Lu et al., "The Identification of Potential Factors Associated with the Development of Type 2 Diabetes," Molecular & Cellular Proteomics, vol. 7(8), pp. 1434-1451 (2008).

Schiff et al., "Electron transfer flavoprotein deficiency: Functional and molecular aspects," *Molecular Genetics and Metabolism*, vol. 88(2), pp. 153-158 (2006).

Wen et al., "Riboflavin-responsive lipid-storage myopathy caused by *ETFDH* gene mutations," *J. Neurol. Neurosurg. Psychiatry*, vol. 81(2), pp. 231-236 (Feb. 2010).

Zhang et al., "cDNA Microarray Analysis of Gene Expression Profiles in Human Fibroblast Cells Irradiated with Red Light," *The Journal of Investigative Dermatology*, vol. 120(5), pp. 849-857 (May 2003).

Office Action issued in Chinese Patent Application No. 201180074671.7, on Apr. 22, 2016.

Search Report issued with Office Action issued in Chinese Patent Application No. 201180074671.7, on Apr. 22, 2016 (English translation only).

Gene ID: 2109, www.ncbi.nlm.nih.gov/gene/2109 (Jul. 31, 2008).

Vaughan et al., "Transforming Growth Factor-β1 Promotes the Morphological and Functional Differentiation of the Myofibroblast," *Experimental Cell Research*, vol. 257, pp. 180-189 (2000).

\* cited by examiner

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial sequence
<220> FEATURE:
<223> OTHER INFORMATION: PCR primer

<400> SEQUENCE: 1
ggggacaagt tgaaagtgga                                           20

<210> SEQ ID NO 2
<211> LENGTH: 20
<212> TYPE: DNA
<213> ORGANISM: Artificial sequence
<220> FEATURE:
<223> OTHER INFORMATION: PCR primer

<400> SEQUENCE: 2
cagagagctt ggaggtcagg                                           20

<210> SEQ ID NO 3
<211> LENGTH: 18
<212> TYPE: DNA
<213> ORGANISM: Artificial sequence
<220> FEATURE:
<223> OTHER INFORMATION: PCR primer

<400> SEQUENCE: 3
```

```
gtggccatcc agctgacc                                          18

<210> SEQ ID NO 4
<211> LENGTH: 23
<212> TYPE: DNA
<213> ORGANISM: Artificial sequence
<220> FEATURE:
<223> OTHER INFORMATION: PCR primer

<400> SEQUENCE: 4
agtggtaggt gatgttctgg gag                                    23

<210> SEQ ID NO 5
<211> LENGTH: 20
<212> TYPE: DNA
<213> ORGANISM: Artificial sequence
<220> FEATURE:
<223> OTHER INFORMATION: PCR primer

<400> SEQUENCE: 5
tgcaccacca actgcttagc                                        20

<210> SEQ ID NO 6
<211> LENGTH: 21
<212> TYPE: DNA
<213> ORGANISM: Artificial sequence
<220> FEATURE:
<223> OTHER INFORMATION: PCR primer

<400> SEQUENCE: 6
ggcatggact gtggtcatga g                                      21

<210> SEQ ID NO 7
<211> LENGTH: 21
<212> TYPE: DNA
<213> ORGANISM: Artificial sequence
<220> FEATURE:
<223> OTHER INFORMATION: PCR primer

<400> SEQUENCE: 7
gggaagaaag acagucggut t                                      21

<210> SEQ ID NO 8
<211> LENGTH: 21
<212> TYPE: DNA
<213> ORGANISM: Artificial sequence
<220> FEATURE:
<223> OTHER INFORMATION: PCR primer

<400> SEQUENCE: 8
accgacuguc uuucuuccct t                                      21
```

METHOD OF IDENTIFYING ABNORMAL CELLS BY EXPRESSION LEVELS OF ETFB

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 17387885_1.TXT, the date of creation of the ASCII text file is Mar. 4, 2014, and the size of the ASCII text file is 68 KB.

TECHNICAL FIELD

The present invention relates to application of the electron transfer flavoprotein beta subunit (ETFB) to cell growth, an agent for suppressing cell growth, and a drug for treatment of abnormal cell growth, which drug comprises the suppressing agent.

BACKGROUND ART

Abnormal growth of fibroblasts are involved in hypertrophic scars formed after injury, and various diseases such as pulmonary fibrosis, cirrhosis and nephrosclerosis. It is said that TGF-β is involved in processes that induce these abnormal growth (see, for example, Patent Document 1, Patent Document 2 and Patent Document 3). However, since TGF-β is a multi-task biological substance, treatment of these diseases by simple suppression of TGF-β has been difficult in many aspects, and it is thought that such a fact is preventing development of an effective TGF-β inhibitor having only small side effects. That is, it is thought that discovery and selective suppression of factors positioned downstream of TGF-β, which factors are responsible for the abnormal growth of fibroblasts directly involved in these diseases, may be an effective means for suppressing the abnormal growth of fibroblasts.

On the other hand, although ETFB is a protein involved in electron transfer (see, for example, Patent Document 4, Patent Document 5, Patent Document 6 and Patent Document 7) and sometimes used as a biomarker, its functions are hardly known. It is reported, for example, that a mutation of ETFB is found in lipid storage myopathy (see, for example, Non-patent Document 1), that ETFB may be a factor involved in type II diabetes (see, for example, Non-patent Document 2), and that ETFB may be a factor involved in multiple acyl-CoA dehydrogenase deficiency (MADD) (see, for example, Non-patent Document 3). However, no function of ETFB is known at all for the skin or fibroblasts. Further, no relationship between ETFB and TGF-β is known.

On the other hand, it has already been reported that, when fibroblasts are cultured under tension in a collagen gel, promoted cell growth, increased expression levels of collagen and the like, and phenomena similar to those observed in fibrosis can observed, and that, in cases where this culture is carried out in the presence of TGF-β, differentiation of fibroblasts into myofibroblasts can be observed (see, for example, Non-patent Document 4). However, no factor for the cell growth in such a phenomenon has been clarified.

PRIOR ART DOCUMENTS

Patent Documents

[Patent Document 1] JP 2010-222351 A
[Patent Document 2] JP 2010-59124 A
[Patent Document 3] JP 2009-40796 A
[Patent Document 4] Japanese Translated PCT Patent Application Laid-open No. 2010-508014
[Patent Document 5] WO2006/054722
[Patent Document 6] Japanese Translated PCT Patent Application Laid-open No. 2010-514441
[Patent Document 7] JP 2010-107461 A

Non-Patent Documents

[Non-patent Document 1] Wen B. et. al., J. Neurol. Neurosurg. Psychiatry. 2010; 81(2):231-6
[Non-patent Document 2] Lu H. et. al., J. Mol. Cell. Proteomics. 2008; 7(8):1434-51
[Non-patent Document 3] Schiff M. et. al., Mol. Genet. Metab. 2006; 88(2):153-8
[Non-patent Document 4] Au K. et. al., Exp. Mol. Pathol. 2010; 89(3):236-240

SUMMARY OF THE INVENTION

The present invention was carried out under such conditions, and aims to provide a method for identifying and suppressing abnormal growth of fibroblasts at an early stage.

In view of this, the present inventors intensively studied in order to find a means for identifying and suppressing abnormal growth of fibroblasts at an early stage. As a result, the present inventors discovered that the expression of ETFB is higher under conditions where fibroblasts are cultured in the presence of tension in a collagen gel compared to cases where fibroblasts are cultured in the absence of tension in a collagen gel, and found that this is a factor for abnormal growth of fibroblasts, thereby completing the present invention.

That is, the present invention is as follows.

<1> A method for identifying the growth state of fibroblasts using as an index the level of expression of ETFB (electron transfer flavoprotein beta subunit), comprising:
judging, in cases where the level of expression of ETFB is high, that there is a high probability that fibroblasts are abnormally growing, and
judging, in cases where the level of expression of ETFB is low, that there is a high probability that fibroblasts are normally growing.

<2> The identification method according to <1>, wherein the cases where the level of expression of ETFB is high are cases where the expression level in fibroblasts of the test sample is higher than the expression level in control fibroblasts, and
the cases where the level of expression of ETFB is low are cases where the expression level in fibroblasts of the test sample is the same as or lower than the expression level in control fibroblasts.

<3> The identification method according to <1>, wherein the abnormal growth of fibroblasts is fibrosis.

<4> The identification method according to <3>, wherein the fibrosis is due to differentiation of fibroblasts into myofibroblasts.

<5> The identification method according to <1>, wherein the abnormal growth of fibroblasts is hypertrophic scar formation.

<6> A method for identifying fibrosis in an organ suspected of having fibrosis, using as an index the level of expression of ETFB in fibroblasts in the organ, comprising:
judging, in cases where the level of expression of ETFB is high, that there is a high probability that the organ has fibrosis; and judging, in cases where no rise in ETFB is found, that there is only a low probability that the organ has fibrosis.
<7> The method for identifying fibrosis in an organ according to <6>, wherein
the cases where the level of expression of ETFB is high are cases where the expression level in the organ of the test sample is higher than the expression level in a control, and the cases where no rise in ETFB is found are cases where the expression level in the organ of the test sample is the same as or lower than the expression level in a control.
<8> The method for identifying fibrosis in an organ according to <7>, wherein the organ is skin.
<9> A method for identifying a fibrosis-suppressing agent, comprising:
culturing fibroblasts under tension in a collagen gel in the presence and absence of a test substance; and
judging the test substance to be a fibrosis-suppressing agent in cases where the expression level of ETFB is lower in the culture in the presence of the test substance than in the culture in the absence of the test substance.
<10> The method for identifying fibrosis-suppressing agent according to <9>, wherein the fibrosis is hypertrophic scar formation.
<11> The method for identifying a fibrosis-suppressing agent according to <10>, wherein the fibrosis is a hypertrophic scar in skin.
<12> The identification method according to any one of <1> to <11>, wherein the expression of ETFB is protein expression.
<13> The identification method according to any one of <1> to <11>, wherein the expression of ETFB is RNA expression.
<14> The identification method according to <13>, wherein the level of expression of ETFB is measured by polymerization chain reaction (PCR).
<15> The identification method according to <14>, wherein the PCR uses primers which are:
the oligonucleotide of SEQ ID NO:1, or an oligonucleotide that has the oligonucleotide of SEQ ID NO:1 as a partial sequence and is capable of amplifying a base sequence encoding ETFB; and
the oligonucleotide of SEQ ID NO:2, or an oligonucleotide that has the oligonucleotide of SEQ ID NO:2 as a partial sequence and is capable of amplifying a base sequence encoding ETFB.
<16> A fibrosis-suppressing agent composed of a test substance, wherein, when fibroblasts are cultured under tension in a collagen gel in the presence and absence of the test substance, the expression level of ETFB is lower in the culture in the presence of the test substance than in the culture in the absence of the test substance.
<17> The fibrosis-suppressing agent according to <16>, wherein the fibrosis is hypertrophic scar formation.
<18> A hypertrophic scar treatment drug comprising as an effective component the fibrosis-suppressing agent according to <16>.
<19> The hypertrophic scar treatment drug according to <18>, for treatment of a formed hypertrophic scar.
<20> The hypertrophic scar treatment drug according to <18>, for prevention of exacerbation of a formed hypertrophic scar.
<21> The hypertrophic scar treatment drug according to <18>, for prevention of formation of a scar that is highly likely to be formed.
<22> An oligonucleotide that is substantially the same as the oligonucleotide shown in SEQ ID NO:1 or 2, and is capable of amplifying a base sequence encoding ETFB.

By the present invention, a method for identifying and suppressing abnormal growth of fibroblasts at an early stage can be provided.

Figure 1:
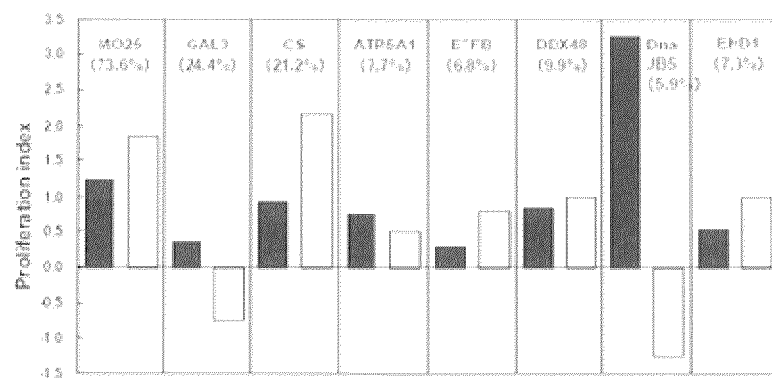
FIG. 1 is a diagram illustrating the results of culture in a collagen gel in Example 1.

DESCRIPTION OF THE EMBODIMENTS (ETFB)
ETFB, which is the main factor of the present invention, is also called the electron transfer flavoprotein beta subunit, an its detailed base sequences are already deposited in gene data banks such as GenBank. For example, a human-type ETFB is deposited in GenBank as CAG33108.1. This was identified by the following procedure as a growth factor for fibroblasts.
In culture for identification of growth factors for fibroblasts, which is carried out under tension load in a collagen gel, fibroblasts show cell growth, increased expression of collagen, and the like. In this growth, the cell morphology and expression of humoral factors are similar to those in fibrosis. On the other hand, without tension load, such a growth phenomenon does not occur. That is, when expressed proteins or RNAs are compared between cases where fibroblasts are cultured in a collagen gel under tension load and cases where fibroblasts are cultured in a collagen gel without tension load to find proteins or RNAs that are expressed only under tension load, proteins or RNAs whose expression is promoted only under tension load are highly likely to be growth factors for fibroblasts or factors for fibrosis. The thus identified proteins or RNAs may be subjected to knockdown experiments using siRNAs or the like, and if suppression of growth of fibroblasts or suppression of fibrosis occurs as a result of the experiments, the proteins or RNAs can be said to be growth factors for fibroblasts or factors for fibrosis.

Therefore, in the present invention, the target may be either a gene such as RNA, or a protein.

For example, in cases where the target is a protein, a culture and/or culture product of fibroblasts may be subjected to a proteome analysis by the DD method (differential display method) or the like. That is, the analysis may be carried out by development by two-dimensional electrophoresis, DD, and identification of the obtained spots by MALDI-TOF-MS. The identified protein is subjected to suppression of its function to see whether there is a possibility of amelioration of pathological conditions. The spatial structure of the target protein is investigated to find its active center, and a compound that fits to the active center with high affinity is designed. In these procedures, DD in a proteome analysis, functional suppression techniques with siRNA or the like, a structural analysis of the target protein using a computer, a study of the active center by biological experiments, and/or the like is/are carried out.

The fibroblasts used in such analyses are not limited as long as they are established cells. Since the final embodiment is human fibroblasts, human fibroblasts may be used. Preferred examples of the human fibroblasts include CCD-1113Sk cells (ATCC No. CRL2439, normal human dermal fibroblasts derived from a black female of 39 years old), CCD-1109Sk (ATCC No. CRL2361, normal human dermal fibroblasts derived from a white male of 21 years old), and CCD-1032Sk (ATCC No. CRL2439, normal human dermal fibroblasts derived from a white neonate). These may be purchased from ATCC or the like. These may be cultured in DMEM medium supplemented with FBS, RPMI medium, or the like.

Further, by identifying a protein by such a proteome analysis, the base sequence of the corresponding gene can be assumed by utilizing genetic information in GenBank or the like. By this, the corresponding c-DNA or RNA can be amplified by PCR. Further, it is also possible to prepare an siRNA and carry out a knockout experiment. By a knockout experiment, whether or not the target protein actually contributes to growth or fibrosis of fibroblasts can be studied.

(Method for Identifying Growth State of Fibroblasts)

By such a process, the present inventors discovered that ETFB is specifically produced by tension load culture of fibroblasts in a collagen gel, more specifically, by culture of the cells in the state where the cells are attached to the side surface or bottom surface of a culture vessel. That is, in culture of fibroblasts in a collagen gel, whether or not abnormal growth of fibroblasts such as fibrosis is promoted can be identified using as an index the amount of ETFB produced.

That is, an embodiment of the present invention is a method for identifying the growth state of fibroblasts using as an index the level of expression of ETFB (electron transfer flavoprotein beta subunit), comprising:

judging, in cases where the level of expression of ETFB is high, that there is a high probability that fibroblasts are abnormally growing, and judging, in cases where the level of expression of ETFB is low, that there is a high probability that fibroblasts are normally growing.

The term "using as an index the level of expression of ETFB" may alternatively be described as "measuring the level of expression of ETFB as a marker".

The term "there is a high probability that fibroblasts are abnormally growing" may alternatively be described as "there is a high risk that fibroblasts are abnormally growing". The term "there is a high probability that fibroblasts are normally growing" may alternatively be described as "there is only a low risk that fibroblasts are abnormally growing". The term "a method for identifying the growth state of fibroblasts" may alternatively be described as "a method for predicting the risk of abnormal growth of fibroblasts".

The cases where the level of expression of ETFB is high means cases where the expression level in the fibroblasts of the test sample is higher than the expression level in control fibroblasts; and the cases where the level of expression of ETFB is low may be cases where the expression level in the fibroblasts of the test sample is the same as or lower than the expression level in control fibroblasts.

The cases where the level of expression of ETFB is high is not limited, and examples of the cases include cases where ETFB is expressed in fibroblasts of the test sample but not expressed in control fibroblasts, and cases where the expression level in the fibroblasts of the test sample is not less than 150%, not less than 300% or not less than 500% with respect to the expression level in control fibroblasts; and the cases where the level of expression of ETFB is low is not limited, and examples of the cases include cases where the expression level in fibroblasts of the test sample is the same as the expression level in control fibroblasts or not more than 70%, not more than 50% or not more than 10% with respect to the expression level in control fibroblasts.

The fibroblasts in the test sample are cells whose growth state needs to be identified, and examples of the cells include, but are not limited to, those derived from mammals such as human, pig, monkey, chimpanzee, dog, cow, rabbit, rat and mouse.

The control fibroblasts may be normal fibroblasts of the subject, normal fibroblasts of an organism species that is the same as or similar to the subject, or established normal fibroblasts. Examples of the established normal fibroblasts include established cells such as those described above.

The level of expression of ETFB may be determined by measuring the expression of the ETFB protein or by measuring the expression of a gene such as an RNA encoding ETFB. The method for measuring the ETFB protein or the gene encoding ETFB in fibroblasts is not limited, and examples of the method include a method in which the cells are homogenized according to a conventional method to obtain a cell extract containing the ETFB protein or the gene encoding ETFB, and the ETFB protein or the gene encoding ETFB contained in the cell extract is measured by a normal measurement method as described below.

In the present invention, the "abnormal growth of fibroblasts" may be a disease condition due to abnormal growth of fibroblasts. The disease condition due to abnormal growth of fibroblasts is not limited, and examples of the disease condition may include fibrosis (more specifically, hypertrophic scars, keloid, scleroderma, pimple scars, pulmonary fibrosis, hepatic fibrosis and the like), and fibrosis due to differentiation of fibroblasts into myofibroblasts.

Another mode of the present invention is a method for identifying fibrosis in an organ suspected of having fibrosis, using as an index the level of expression of ETFB in fibroblasts in the organ, comprising:

judging, in cases where the level of expression of ETFB is high, that there is a high probability that the organ has fibrosis; and judging, in cases where no rise in ETFB is found, that there is only a low probability that the organ has fibrosis.

The term "there is a high probability that the organ has fibrosis" may alternatively be described as "there is a high risk that the organ has fibrosis". The term "there is only a low probability that the organ has fibrosis" may alternatively be described as "there is only a low risk that the organ has fibrosis". The term "a method for identifying fibrosis in an organ" may alternatively be described as "a method for predicting the risk of fibrosis in an organ".

The cases where the level of expression of ETFB is high may be cases where the expression level in the organ of the test sample is higher than the expression level in a control; and the cases where no rise in ETFB is found may be cases where the expression level in the organ of the test sample is the same as or lower than the expression level in a control.

The cases where the level of expression of ETFB is high is not limited, and examples of the cases include cases where ETFB is expressed in the organ of the test sample but not expressed in a control, and cases where the expression level in the organ of the test sample is not less than 150%, not less than 300% or not less than 500% with respect to the expression level in a control; and the cases where the level of expression of ETFB is low is not limited, and examples of the cases include cases where the expression level in the organ of the test sample is the same as the expression level in a control or not more than 70%, not more than 50% or not more than 10% with respect to the expression level in a control.

The organ of the test sample is an organ whose fibrosis needs to be identified, and examples of the organ include, but are not limited to, organs of mammals such as human, pig, monkey, chimpanzee, dog, cow, rabbit, rat and mouse. The test sample may be cultured cells, a cultured tissue, blood or the like obtained from the subject organ.

The control may be a normal portion of the same or another organ, an organ or cells of an organism species that is the same as or similar to the subject, or established normal cells. Examples of the established normal cells include established cells such as those described above.

The "organ" as the subject of the method of the present invention for identification of fibrosis in an organ is not limited, and examples of the organ include organs such as the skin, lung and liver.

The level of expression of ETFB may be determined by measuring the expression of the ETFB protein or by measuring the expression of a gene such as an RNA encoding ETFB. The method for measuring the ETFB protein or the gene encoding ETFB in fibroblasts of the organ is not limited, and examples of the method include a method in which the cells are homogenized according to a conventional method to obtain a cell extract containing the ETFB protein or the gene encoding ETFB, and the ETFB protein or the gene encoding ETFB contained in the cell extract is measured by a normal measurement method as described below.

(Method for Identifying Agent for Suppressing Abnormal Growth)

Application of the method of the present invention to identification of the growth state of fibroblasts enables judgment of whether a test substance is an agent for promoting abnormal growth or an agent for suppressing abnormal growth, based on observation of whether production of ETFB increases or decreases in the presence of the test substance.

The abnormal growth herein may be a pathological condition due to abnormal growth of fibroblasts. The pathological condition due to abnormal growth of fibroblasts is not limited, and examples of the pathological condition may include fibrosis (more specifically, hypertrophic scars, keloid, pimple scars, scleroderma, pulmonary fibrosis, hepatic fibrosis and the like), and fibrosis due to differentiation of fibroblasts into myofibroblasts.

An embodiment of the present invention is a method for identifying a fibrosis-suppressing agent, comprising:

culturing fibroblasts under tension in a collagen gel in the presence and absence of a test substance; and judging the test substance to be a fibrosis-suppressing agent in cases where the expression level of ETFB is lower in the culture in the presence of the test substance than in the culture in the absence of the test substance.

The cases where the level of expression of ETFB is lower in the culture in the presence of the test substance than in the culture in the absence of the test substance is not limited, and examples of the cases include cases where ETFB is not expressed in the presence of the test substance, and cases where the expression level of ETFB in the presence of the test substance is not more than 70%, not more than 50% or not more than 10% with respect to the expression level in the absence of the test substance.

The culture conditions for the culture in a collagen gel in the presence and absence of the test substance are not limited, and may be conditions where the negative control cells grow well and the difference in the cell growth is clear between the cultures in the presence and absence of the test substance. For example, the culture may be carried out in a gel containing 0.05 to 0.5 wt % collagen at 30 to 40° C. for 12 to 72 hours.

The "method for identifying a fibrosis-suppressing agent" may alternatively be described as the "method for screening a fibrosis-suppressing agent".

The test substance may be either a natural product or a synthetic product, and may be a substance that can be a candidate for a normal pharmaceutical or the like. Specific examples of the test substance include extracts derived from plants and microorganisms, and their purified products; low-molecular synthetic compounds; antibodies; peptides; aptamers; siRNAs; nucleic acids used for gene therapy; and modified products and derivatives thereof In such identification, ETFB may be quantified as a protein, or may be quantified as a gene such as an RNA encoding ETFB. As the method for quantifying the protein or gene, a conventional method may be used. Examples of the measurement method include gel electrophoresis; Western blotting; immunoassays such as ELISA; immunohistochemical analysis; Northern blotting; and PCR. Quantification of the gene such as RNA is especially preferred since the amplification method by PCR is applicable thereto.

In cases where ETFB is quantified as a protein, a reagent with which proteins in a gel can be stained, or an antibody that specifically recognizes ETFB may be used. The antibody may be either a monoclonal antibody or polyclonal antibody. These antibodies can be produced by a known method. If necessary, the antibody may be labeled with a fluorescent dye, radioactive isotope, enzyme or the like.

In cases where ETFB is quantified as a gene, the quantification may be carried out using a pair of nucleic acid primers composed of a nucleic acid primer that can specifically hybridize with mRNA of ETFB and a nucleic acid primer that can specifically hybridize with cDNA synthesized using the mRNA as a template. The primers may be designed based on the sequence information for the gene to be measured.

For example, as a primer for carrying out the PCR reaction, the oligonucleotide shown in SEQ ID NO:1 of SEQUENCE LISTING or the oligonucleotide shown in SEQ ID NO:2 of SEQUENCE LISTING may be used. An oligonucleotide having a similar effect, that is, an oligonucleotide that comprises such a sequence as its partial sequence and can amplify a base sequence encoding ETFB is included within the technical scope of the present invention. The length of the oligonucleotide is not limited, and, for example, the length is about 10 to 50 bases or about 15 to 30 bases.

(Agent for Suppressing Abnormal Growth)

A test substance that was evaluated as described above and found to have a suppressive action on ETFB expression can be judged to be an agent for suppressing abnormal growth of fibroblasts. Such an agent for suppressing abnormal growth of fibroblasts may be made into a skin external drug containing the suppressing agent, or may be manufactured into a pharmaceutical composition to provide a pharmaceutical for prophylaxis or treatment of diseases caused by abnormal growth of fibroblasts, such as scars, especially hypertrophic scars. Examples of uses as a prophylactic agent that can be preferably disclosed include prevention of formation of a hypertrophic scar by preliminarily administering the agent at a site where a scar, especially hypertrophic scar, is highly likely to be formed, such as the vicinity of a site of surgical excision, before formation of the hypertrophic scar; and prevention of exacerbation of a formed hypertrophic scar by preliminarily administering the agent. Preferred examples of uses of the agent in therapy include reduction of a scar such as an already formed hypertrophic scar, by administration of the agent to the scar. In terms of formulation of the pharmaceutical, the pharmaceutical may be manufactured into a pharmaceutical formulation by blending the agent for suppressing abnormal growth of fibroblasts with an arbitrary component(s) for formulation such as a vehicle, disintegrator, binder, coloring agent, corrigent, corrective, dispersant and/or surfactant, and processing the resulting product according to a conventional method. Possible examples of the dosage form of the pharmaceutical formulation include internal medicines, external medicines and injection solutions. The pharmaceutical formulation is especially preferably an external medicine.

A sample collected from a living body such as a skin section may be subjected to investigation of the level of expression of ETFB in the sample by PCR or the like to know how likely a scar will be formed in the vicinity of the site where the sample was collected.

The present invention is described below in more detail by way of an Example.

EXAMPLE 1

(Cell Culture)

Although a number of types of normal human dermal fibroblasts are available from ATCC, CCD-1113Sk cells (derived from a black female of 39 years old), which have a profile closest to a keloid cell line (KELFIB), were preferentially used.

The fibroblasts were cultured in DMEM (D-6046, Sigma) supplemented with 10% FBS in a tissue culture flask (353024, BD FALCON) placed in an incubator (M14-3158, Form a Scientific, SANYO) at 37° C. under 5% $CO_2$. Upon subculture, the cells were washed with PBS, and 0.05% trypsin solution (T4049, Sigma) was added to the cells, followed by incubating the resultant for 2 to 3 minutes in an incubator, collecting the cells, and then performing subculture. The subculture was carried out every 3 to 4 days, and the passage number was 7 to 12 in this case.

(Cell Culture in Collagen Gel)

The culture of cells in a collagen gel was carried out according to a modification of the method by Varedi et al. That is, DMEM (5×DMEM, D5523, Sigma) having the concentration 5 times higher than the normal concentration was prepared using a powder medium, and a collagen solution was prepared at the following mixing ratio such that the composition of DMEM medium was finally attained. The prepared collagen solution was stored in a thermostat at 12° C. until use. A required amount of a stock collagen solution (7 mL in cases where the concentration is 1 mg/mL), 7 mL of 5×DMEM, 3.5 mL of 200 mM HEPES, 3.5 mL of 0.03% $NaH_2CO_3$, 1.5 mL of 0.01% NaOH and a required amount of FBS (3.5 mL in cases where the concentration is 10%) were mixed together, and $H_2O$ was added to the resulting mixture to attain a final volume of 31.5 mL. When a basal layer was prepared, 250 µL or 1 mL of the collagen solution was preliminarily placed in a 24-well or 6-well tissue culture plate (24-well plate, 353047; 6-well plate, 353046; BD FALCON), respectively, and the solution was left to stand in an incubator for not less than 15 minutes to solidify the collagen.

A cell suspension at a density of $1\times10^6$ cells/mL was prepared, and mixed with the collagen solution stored at 12° C. at a mixing ratio of collagen solution:cell suspension of 9:1, followed by stirring the resulting mixture well, immediately seeding the cells, and transferring the plate to an incubator. The amount of cells seeded was 1 mL in the case of a 24-well plate, or 4 mL in the case of a 6-well plate ($1\times10^5$ cells/mL in both cases). When a floating gel was prepared, culture was carried out for 2 hours in the incubator and then the gel was released from the rim of the well using a spatula, followed by continuing the culture.

(Measurement of Cell Number)

After the culture for a predetermined period of time in each experiment, the collagen gel was detached from the plate using a spatula, and the detached gel was placed in a collagenase solution prepared using DMEM such that the final concentration was 310 U/mL. Collagen was digested by incubation at 37° C. for 20 to 40 minutes with shaking. The cell suspension after digestion was centrifuged at 1500 rpm for 3 to 5 minutes to collect the cells. To the collected cells, 100 µL of a medium was added, and the cells were stained with trypan blue. Thereafter, the number of living cells was counted using a Burkel-Turk hemacytometer at a dilution rate of 1/5.

(TUNEL Staining)

Collagen in the collagen gel was digested and the cells were recovered. Thereafter, 1 mL of DMEM medium and a cell fixation liquid (Collection Fluid, 6768315, Thermo Shandon) were added to the cells, and the cells were mixed by inversion. The resulting cell suspension was centrifuged using Cytospin (Thermo scientific), and the cells were attached to a slide glass to prepare a sample. The prepared sample was subjected to TUNEL staining using in situ Apoptosis Detection Kit (MK500, Takara) according to the manufacturer's instructions. Positive cells appeared in the attached state and in the detached state were observed under the microscope using a fluorescence microscope (ECLIPSE E600, Nikon) at a magnification of ×100 to ×400.

(Two-Dimensional Electrophoresis)

For each of the cultures in the attached state and the detached state, 8 to 10 collagen plates were prepared, and collagen was digested on Day 1 of the culture in the same manner as described above. However, for suppressing non-specific protein degradation by collagenase as much as possible, the digestion was carried out in the presence of 1 mM benzamidinehydrochrolide hydrate (B6506, Sigma) and 0.1 mM N-α-p-tosyl-L-lysine chloromethylketone hydrochloride (TLCK, T7254, Sigma).

The cells after digestion was collected into an Eppendorf tube by centrifugation, and washed twice with PBS. This operation was carried out on ice as much as possible. The wet weight of the cells was 100 to 200 mg at this time. The membrane fraction was extracted using ProteoPrep Membrane Extraction Kit (Sigma) according to the manufacturer's instructions. For thawing of the cells, a protease inhibitor (Protease Inhibitor Cocktail, P2714, Sigma) and a phosphatase inhibitor (Phosphatase inhibitor cocktail I&II, P2850&P5726, Sigma) were added according to the manufacturer's instructions. The amount of the extracted protein was measured using Coomassie Protein Assay Reagent Kit (2320, PIERCE) according to the manufacturer's instructions, and the protein was stored in a deep freezer until use. The extraction rate (the amount of membrane protein obtained per wet weight of the cells) per extraction was about 1/300.

Two-dimensional electrophoresis was carried out using a two-dimensional electrophoresis apparatus manufactured by Pharmacia. Isoelectric focusing was carried out using a 18-cm gel (Immobile Dry Strip, Amersham) in pI ranges of: 3 to 10 NL (non-linear); 5.5 to 6.7; and 6 to 9. The amount of protein applied was 100 to 300 μg. In the isoelectric focusing, development was carried out by the cup loading method according to the manufacturer's instructions. As the electrophoresis apparatus, Ettan IPGphor IEF System(Amersham) was used, and the conditions for development were as follows.

50 μA/Strip, 20° C.
S1: Gradient 500 V, 1 min.
S2: Gradient 4000 V, 4 h
S3: Step-n-hold 8000 V, 10 h
S4: Step-n-hold 6000 V, until recovery Thereafter, SDS-PAGE was carried out using Multiphor II electrophoresis unit (18-1018-06, Amersham) and Electrophoresis Power supply (19-3500-01, Amersham). As the gel, a precast gel (Excel-Gel SDS, 80-1255-53, Amersham, 245×110 mm, 0.5 mm thin, Gradient 8-18%) was used, and the electrophoresis was carried out under the conditions of: S1: 600 V, 400 mA, 13 W, 30 min.; S2: 600 V, 400 mA, 30 W, 16 h. The gels after development were subjected to silver staining using an automatic staining apparatus (Hoefer Processor Plus, Amersham) and Silver stain MS kit (299-58901, Wako Pure Chemical Industries, Ltd.) according to the manufacturer's instructions such that the same staining conditions were attained among the gels. The developing time was 6 minutes. The above operation was repeated to prepare 5 gels for each of the attached state and the detached state in the above-described pI ranges. Until use in the MALDI-TOF-MS analysis, the gels were stored in 8.7% glycerol at 4° C.

(Differential Display Analysis)

The gels after staining were scanned using a scanner (ImageScanner III, 28-9076-07, Amersham) and the obtained images were stored in a computer. The obtained images were analyzed using an image analysis software (2D Master Elite Ver. 4.01, 2D Master Database Ver. 4.00, Amersham) by the following procedure. The whole procedure of DD was as shown below.

(1) Automatic detection of spots by the computer, and corrections for overlapping spots by visual observation
(2) Standardization among the gels in terms of the background that were not detected as spots, and of the staining intensity of the whole stained spots
(3) Numbering of spots that were recognized to be common among the gels based on the mobility (matching, each of the numbers detected by this process is referred to as Match No.), and statistical analysis to see whether the electrophoretic profiles of the same sample are truly equivalent to each other (gels judged to be equivalent to each other in this process were subjected to DD)
(4) DD by t-test (rejection rate, 10%)

Further, DD by visual observation was carried out at the same time to judge whether the spots identified by the processing by the computer truly had different staining intensities, and to further include spots whose intensities were not significantly different from each other based on the processing by the computer but were different from each other based on the visual observation.

<1> Detection of Spots

Each image captured with ImageScanner III was trimmed to adjust its size. Automatic detection of spots was carried out using 2D Master Elite with the following parameters.

Peak Dilation Parameters:
Min. Peak Area, 85
Max. Peak Area, 1100
Min. Aspect Ratio, 0.4
Max. Aspect Ratio, 4.5
Min. Area Ratio, 50

<2> Background Subtraction and Standardization of Spot Intensities

The setting for background subtraction provided in 2D Master Elite, and the operation of standardization of the staining intensities of scanned gels were carried out according to the manufacturer's instructions.

Max. Number of Touching Peaks, 20
Background Intensity, 0
Step Size, 1
Smoothing Size, 1
Histogram Equalization, No
Tidy Edges, Yes Thereafter, the spots were visually observed and corrections for multiply-detected spots were made.

<3> Spot Matching and Judgment of Equivalence Among Gels

A gel in the detached state whose image showed a large number of clear spots was used as the reference gel, and matching of spots was performed according to the manufacturer's instructions. Using the Test Hypothesis function provided in 2D Master Database, a Dunnett test with the reference gel was carried out. The groups in which not less than 3 out of the 5 gels were found to be equivalent to each other were subjected to the operation of <4>.

<4> DD of Cultured Cells in Attached State and Detached State

Using 2D Master Database, matched spots were subjected to a t-test with a rejection rate of 10% to extract spots exhibiting different intensities. Thereafter, the identified spots were visually observed to confirm that the difference can also be found visually. At the same time, the whole spots were visually observed again to further include spots that were not detected by the processing by the computer but show difference in the intensity between the attached state and the detached state.

The spots that were found to show difference in the expression level by the above-described technique were subjected to MALDI-TOF-MS analysis. From 3 to 4 gels judged to be equivalent, the spots having higher expression levels were cut out. Since the amount of protein was expected to be small, these gel pieces were combined and subjected to the test as a single sample. Desilverization and digestion with trypsin were carried out using a 96-well trypsin digestion device and a kit (Montage In-Gel Digest Kit, Millipore) according to the manufacturer's instructions. The protein after trypsin digestion was spotted in an amount of 1 μL on an anchor chip (74115, Bruker Daltonics Inc.) together with a matrix (CHCAmatrix; 10 mg/mL α-CHCA in acetone-Ethanol 1:1 v/v). After drying, the protein was subjected to Peptide Mass Fingerprinting (PMF) analysis using MALDI-TOF-MS (AutoFlex II, Bruker Daltonics Inc.). The PMF analysis is a method for assuming a protein based on the mass pattern of peptide fragments that fly out from a matrix. Spots containing a sufficient amount of protein were subjected to identification of the protein by Post Source Decay (PSD) analysis, which is a pseudo-MS/MS analysis and capable of analyzing the amino acid sequence. The results obtained by PMF analysis were subjected to database search, in which MASCOT (Ver.1.9, Matrix science) was used as the database and each protein was determined when the probability was not less than 95% according to the score distribution by the MOWSE algorithm and the molecular weight and the isoelectric point calculated in MASCOT were equivalent. In the PSD analysis, the above database was used to search for a candidate based on the amino acid sequence, and a protein with an equivalent molecular weight and isoelectric point was determined to be the corresponding protein. Under the present experiment conditions, the lower detection limit by the PMF analysis using BSA was 5 fmol.

Determination of proteins from a total of 31 spots were attempted. Lists of the proteins determined by MALDI-TOF-MS are shown in Tables 1 and 2. Among the total of 31 spots, proteins could be determined from 18 spots (8 spots in the neutral region and 10 spots in the basic region). Among these, 8 proteins showed higher expression levels in the attached state, 9 proteins showed higher expression levels in the detached state, and 1 protein was considered to be due to spot shift. Nine proteins were proteins localized in the membrane; 2 proteins were proteins localized in the nucleus; 3 proteins were proteins localized in the cytoplasm; 1 protein was a secretory protein; and localization of 3 proteins was unknown. Although no protein for the outer membrane was obtained, intracellular membrane proteins were obtained to some extent, and two types of chaperones that can be obtained from total protein in large amounts were obtained. Thus, it was considered that the fractionation was effective. Among the 8 proteins that showed higher expression levels in the attached state, 3 proteins were proteins localized on the mitochondrial membrane; 2 proteins were proteins present in the nucleus; 1 protein was a protein localized in the membrane; and localization of 2 proteins was unknown. Among the obtained proteins, the following proteins have been reported to be involved in wound healing or wound formation: citrate synthase has been reported to show increased expression within 10 days after formation of a wound; Galectin-3 knockout mice have been reported to show delay of re-epithelialization after wounding of cornea; and ETFB has been reported to show increased expression when fibroblasts are irradiated with low-power red light. Involvement of other proteins in wound healing or wound formation was unknown.

TABLE 1

| Match No. | Day (pI range) | Difference | MW (kD) | Calculated pI | Name | Other name | NCBI protein accession No. (nucleotide No.) | SWISS-PROT No |
|---|---|---|---|---|---|---|---|---|
| 203 | Day 1 (5.5-6.7) | A > D | 60.6 | | EH-domain containing protein | Testilin hPAST1 | NP_006786 (NM_006795) | Q9H4M9 |
| 287 | Day 1 (5.5-6.7) | A > D | 46.9 | | Probable ATP-dependent helicase DDX48 | DEAD-box protein 48 Eukaryotic initiation factor 4A-like NUK-34 hNMP 265 | CAA56074 (X79538) | P38919 |
| 416 | Day 1 (5.5-6.7) | A > D | 39.1 | | DnaJ homolog subfamily B member5 | Heat shock protein Hsp40-3 Heat shock protein cognate 40 Hsc40 Hsp40-2 | NP036398 (NM012266) | O75953 |
| 282 | Day 1 (5.5-6.7) | D > A | 55.8 | | AKT3 (short splice form) | EC 2.7.1.- RAC-PK-gamma Protein kinase Akt-3 Protein kinase B, gamma PKB gamma STK-2 | short splice form: T17287, variant2 NP_859029(NM_181690), variant NP_005456(NM | Q9Y243 (isoform: Q9Y243-2) |
| 459 | Day 1 (5.5-6.7) | D > A | 25 | | Peroxnedoxin 6 | Antioxidant protein 2 1-Cys PRX Acidic calcium-independent phospholipase A2 aiPLA2 EC 1.11.1.7 NSGPx | BAA03496 (D14662) | P30041 |
| 290 | Day 1 (5.5-6.7) | D > A | 107.8 | | VPS 11 protein | hVPS11 PP3476 | AAH12051 (BC012051), NP_068375 (NM_021729) | Q9H270 |

TABLE 1-continued

| Match No. | Day (pI range) | Difference | MW (kD) | Calculated pI | Name | Other name | NCBI protein accession No. (nucleotide No.) | SWISS-PROT No |
|---|---|---|---|---|---|---|---|---|
| 168 | Day 1 (5.5-6.7) | Spot shift | 146.2 | | JNK-associated leucine-zipper protein | z | NP_003962 (NM_003971) | Q8IZX7 |
| 123 | Day 1 (6-9) | A > D | 59.8 | | ATP synthase alpha chain mitochondrial | EC 3.6.3.14 | NP_004037 (NM_004046) | P25705 |

TABLE 2

| Match No. | Day (pI range) | Difference | MW (kD) | Calculated pI | Name | Other name | NCBI protein accession No. (nucleotide No.) | SWISS-PROT No |
|---|---|---|---|---|---|---|---|---|
| 175 | Day 1 (6-9) | A > D | 51.7 | | Citrate synthase, mitochondrial [Precursor] | EC 2.3.3.1 | O75390, AAC25560 (AF047042) | O75390 |
| 331 | Day 1 (6-9) | A > D | 27.8 | | Electron-transfer-flavoprotein beta-subunit | Beta-ETF | NP_001976 (NM_001985) | P38117 |
| 326 | Day 1 (6-9) | A > D | 26.2 | | Galactin-3 | Galactose-specific lectin3 MAC-2 antigen IgE-binding protein 35 kDa lectin Carbohydrate binding protein 35 CBP 35 Laminin-binding protein Lectin L-29 L-31 | AAA35607 (M57710) | P17931 |
| 201 | Day 1 (6-9) | A > D | 39.9 | | MO25 protein | CGI-66 | AAD34061 (AF151824) | Q9Y376 |
| 143 | Day 1 (6-9) | D > A | 46.4 | | Colligin 1 | 47 kDa heat shock protein [Precursor] Collagen-binding protein 1 | CAA4379.5 (X61598) | P29043 |
| | | | | | Colligin 2 | Collagen-binding protein 2 [Precursor] Rheumatoid arthritis related antigen RA-A47 | BAA11829 (D83174) | P50454 |
| 425 | Day 1 (6-9) | D > A | 32.4 | | Syntenin 1 | Syndecan binding protein 1 Melanoma differentiation associated protein-9 Mda-9 Scaffold protein Pbp1 Pro-TGF-alpha cytoplasmic domain-interacting protein 18 TACIP18 | NP_005616(NP_005625) | O00560 |
| 389 | Day 1 (6-9) | D > A | 18 | | Peptidyl-prolyl cis-trans isomerase A | EC 5.2.1.8 PPIase Rotamase Cyclophilin A Cyclosporin A-binding protein | NP_066953(NM_021130) | P05092 |
| 95 | Day 1 (6-9) | D > A | 59.4 | | T-complex protein 1, eta subunit | TCP-1-eta CCT-eta HIV-1 Nef interacting protein | AAH19296 (BC019296) | Q99832 |
| 105 | Day 1 (6-9) | D > A | 56 | | UDP-glucose 6-dehydrogenase | EC 1.1.1.22 UDP-Glc dehydrogenase UDP-GlcDH UDPGDH | AAH22781 (BC022781) | O60701 |
| 193 | Day 1 (6-9) | D > A | 78.2 | | Lactotransferrin [Precurso] | Lactoferrin | 1N76A, CAA37914 (X53961) | P02788 |

(Test for Confirmation of Suppressive Effect and Specificity of siRNA)

CCD-1113sk cells (ATCC No. CRL2439, normal human dermal fibroblasts derived from a black female of 39 years old) were used as in the case described above, and the cells were maintained in the same manner as in the above-described method. As the introducing reagent, Lipofectamine 2000 (LF2000, 11668019, Invitrogen) was used according to the manufacturer's instructions. Upon the introduction, OPTI-MEM (31985062, Invitrogen) was used as the medium. LF2000 is a cationic liposome. It forms a complex with an anionic siRNA and incorporated into a cell via an endosome or lysosome. The siRNAs described in Table 3 were used, and siRNAs other than Galectin-3 were purchased. Galectin-3 was designed using the siRNA Design Support System (http://www.takara-bio.co.jp/rnai/intro.htm) available in the HP of Takara. In use of the siRNAs, CCD-1113sk cells prepared by monolayer culture for 1 day after the transfection were used to observe suppression of expression of mRNA using QuantiGene. For confirmation of the specificity of each siRNA used, BLAST (http://blast.ncbi.nlm.nih.gov/Blast.cgi) search was carried out to find a sequence on which the siRNA acts, and mRNA in the same sample was measured using a QuantiGene probe for the gene having a similar sequence. Only siRNAs that did not exhibit a suppressive effect in this experiment were used. As a negative control, Silencer Negative control siRNA #1 (4611, Ambion) was used.

TABLE 3

| Name | siRNA manufacturer | Product No. | Specificity confirmation gene |
|---|---|---|---|
| EH-domain containing protein 1 (EHD1) | Dharmacon | D-019022-01-0010 | Dedicator of cytokinesis 4 (DOCK4) |
| Probable ATP-dependent helicase DDX48 (DDX48) | Dharmacon | D-020762-01-0010 | Protein kinase, cAMP-dependent, regulatory, type I, alpha (tissue specific extinguisher 1) (PRKAR1A), transcript variant 1 |
| DnaJ homolog subfamily B member5 (DnaJB5) | Dharmacon | D-016492-03-0010 | Caspase 8, apoptosis-related cysteine protease (CASP8), transcript variant C |
| ATP synthase alpha chain, mitochondrial (ATP5A1) | Dharmacon | D-017064-03-0010 | Homo sapiens pleiomorphic adenoma gene-like 1 (PLAGL1), transcript variant 1 |
| Citrate synthase, mitochondrial (CS) | Dharmacon | D-009334-01-0010 | None |
| Electron-transfer-flavoprotein beta-subunit (ETFB) | Dharmacon | D-010494-04-0010 | Homo sapiens histone deacetylase 1 (HDAC1) |
| Galectin-3 (GAL3) | Takara | Prepared Sense: GGGAAGAAAGA CAGUCGGUTT (SEQ ID NO: 7) Antisense: ACCGACUGUCU UUCUUCCCTT (SEQ ID NO: 8) | Leucine-rich PPR-motif containing (LRPPRC) |
| MO25 protein | Dharmacon | D-015407-03-0005 | None |

In the above test for confirmation of the suppressive effect and the specificity of the siRNA, 2.5×10⁴ CCD-1113sk cells were cultured in a 12-well plate on the previous day, and introduction of the siRNA was carried out using LF2000 according to the manufacturer's instructions. The amount of LF2000 used was 4 µL/well in terms of the final concentration; the siRNA was used at 33 nM; and the amount of medium was 2 mL. The culture was continued for 1 additional day, and 1 mL of Lysis Buffer (QG0503, Panomics) was added to the culture to provide a sample for measurement using QuantiGene. The sample was stored in a deep freezer until use. Treatment with QuantiGene was carried out according to the manufacturer's instructions, and the measurement was carried out for n=2 per sample. The measurement was carried out using a plate reader (AR-VO.SX, Wallac, PerkinElmer), and measurement of chemiluminescence was carried out at 45° C. The suppression rate was calculated according to the Equation 1 below. Only samples that have a target gene suppression rate of not more than 20% and do not suppress the specificity confirmation gene were used.

Suppression rate (%)=(chemiluminescence value of target gene upon introduction of target gene siRNA−background value)/(chemiluminescence value of GAPDH upon introduction of target gene siRNA−background value)    Equation 1

In the culture in a collagen gel, $1.5 \times 10^5$ CCD-1113sk cells/10-cm dish (353003, FALCON) were seeded, and culture was performed overnight, followed by using LF2000 according to the manufacturer's instructions for transfection with the siRNA. One day later, culture in a collagen gel was carried out using these cells in the same manner as described above (n=2 per time point per gene). During the period from the beginning of the culture in a collagen gel to 4 days after the culture, the number of cells in the gel was counted daily. The counting of the number of cells was carried out by the method described above. Each group of cells used for the counting on the first day of the culture and 3 to 4 days after the culture were collected, and 100 µL of Lysis Buffer was added thereto, followed by measurement of mRNA using QuantiGene. For QuantiGene, the probes shown in Table 4 below were purchased and used.

TABLE 4

| Gene name | Product No. |
|---|---|
| EHD1 | PA-17862 |
| DOCK4 | PA-19178 |
| DDX48 | PA-19202 |
| PRKAR1A | PA-11375 |
| DnaJB5 | PA-18416 |
| CASP8 | PA-11164 |
| ATP5A1 | PA-15833 |
| PLAGL1 | PA-14889 |
| CS | PA-15857 |
| ETFB | PA-14402 |
| HDAC1 | PA-11657 |
| GAL3 | PA-103300 |
| LRPPRC | PA-24579 |
| MO25 | PA-20073 |
| GAPD | PA-10382 |

Figure 2:
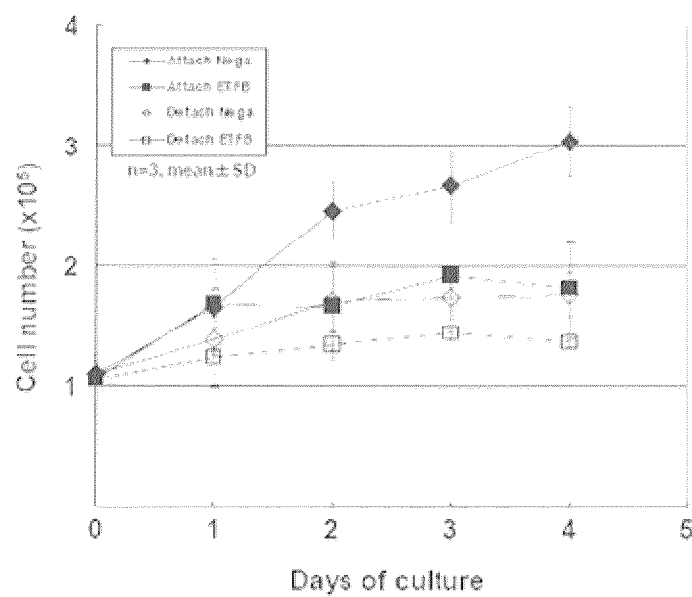
FIG. 2 is a diagram illustrating the influence of ETFB of Example 1 on growth of fibroblasts.

Based on the results described above, identification of proteins that suppress abnormal growth of fibroblasts was carried out by transfection with siRNAs. That is, an siRNA for each protein was purchased, and, after 24 hours of culture in a 10-cm² Petri dish, siRNA transfection treatment was carried out, followed by performing culture in a collagen gel 24 hours later. The results are shown in FIG. 1. The black bars indicate the results obtained for the attached state and the white bars indicate the results obtained for the detached state. GAL3, EHD1 and ETFB were factors that showed suppression of the cell growth in the attached state. DnaJB5 was found to increase the cell number by promotion of the growth. On the other hand, in the detached state, GAL3 and DnaJB5 were found to decrease the cell number, and therefore their cytotoxicity was suggested. MO25 and CS were found to promote the cell growth. GAL3 was found to suppress the cell growth in the attached state, but, since a decrease in the cell number was found in the detached state, there was a possibility that the suppression of cell growth was due to cytotoxicity. Therefore, GAL3 was excluded from the candidates. On the other hand, EHD1 and ETFB did not cause a remarkable decrease in the cell number even in the detached state, and showed suppression of the cell growth in the attached state. Thus, in order to confirm reproducibility of the results on the 2 factors, a more detailed test was carried out. As a result, the results on EHD1 were not reproducible. On the other hand, ETFB showed suppression of the cell growth in the attached state as compared to the negative control, and the cell number did not remarkably decrease in the attached state (see FIG. 2), so that a similar tendency was observed. Thus, the results were reproducible.

(Knockdown Experiment with siRNA)

In order to investigate the function of the above-described ETFB, a knockdown experiment was carried out using an siRNA. That is, CCD-1113sk cells (ATCC No. CRL2439, normal human dermal fibroblasts derived from a black female of 39 years old) were used and maintained in the same manner as described above. The siRNA and the introduction reagent used were the same as those described above. As a negative control, Silencer Negative control siRNA #1 (4611, Ambion) or AllStars Negative Control siRNA (Cat. No. 1027281, QIAGEN) was used. The method of introduction was the same as the method described above.

In the cases where TGF-β was added, Human rTGF-β1 (100-B-010, R&D Systems) was added upon preparation of a collagen solution, and the resulting mixture was mixed, followed by seeding the cells.

For measurement of mRNA, qRT-PCR was carried out. That is, from the cells recovered in each experiment, total RNA was purified using RNeasy mini kit (74104, QIAGEN) according to the manufacturer's instructions. From 0.1 µg of the RNA, cDNA was prepared using QuantiTect Reverse Transcription Kit (205311, QIAGEN) according to the manufacturer's instructions. Using QuantiTect SYBR GreenPCR Kit (204145, QIAGEN) and a real-time PCR machine (ABI PRISM 6700, Applied Biosystem Inc.), 5 µL of the cDNA was analyzed to measure the mRNA expression level. Triplicate measurements were carried out, and measurement of the expression level of GAPD was carried out at the same time. The primers described in Table 5 below were used. Collagen gel culture was carried out, and images of the 24-well plate were captured using a scanner (Multiscanner III, Amersham) from Day 0 of the culture. After the capture, the area of the gel in the well was measured using NIH Image. The area of the bottom of the well was regarded as 100%, and the percentage of the measured area was calculated.

TABLE 5

| Gene name | Prepared/Purchaseed | Sequence Product name |
|---|---|---|
| Collagen 1A1 | Produced with PRIMER3 | Forward: GTGGCCATCCAGCTGACC (SEQ ID NO: 3) Reverse: AGTGGTAGGTGATGTTCTGGGAG (SEQ ID NO: 4) |
| ETFB | Produced with PRIMER3 software | Forward: GGGGACAAGTTGAAAGTGGA (SEQ ID NO: 1) Reverse: CAGAGAGCTTGGAGGTCAGG (SEQ ID NO: 2) |
| Alpha smooth muscle actin (SMA) | Purchased | QuantiTect primer assay (QT00088102, Unpublished sequence) |
| GAPD | Prepared by reference to literature [#60] | Forward: TGCACCACCAACTGCTTAGC (SEQ ID NO: 5) Reverse: GGCATGGACTGTGGTCATGAG (SEQ ID NO: 6) |

Figure 3:
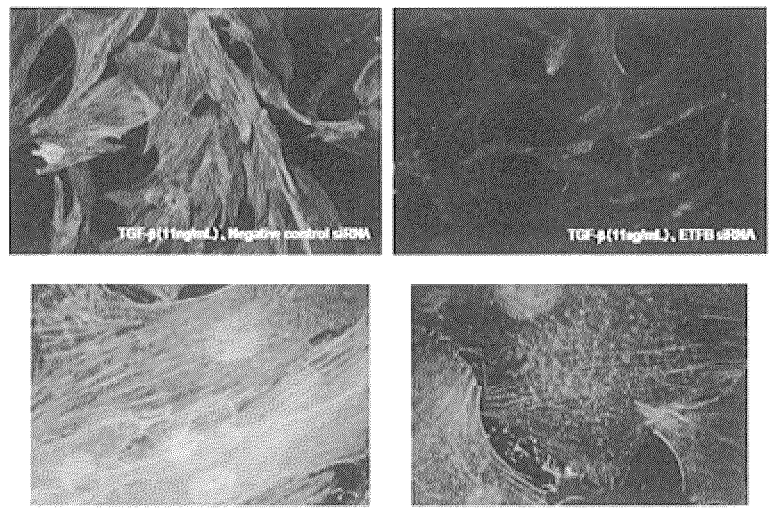
FIG. 3 is a diagram (photographs) illustrating the influence of an ETFB siRNA on stress fiber formation induced by TGF-β of Example 1. After introduction of the ETFB siRNA or a negative control siRNA into CCD-1113sk cells, TGF-β (11 ng/ml) was added to the cells, and the cells were then cultured for 3 days, followed by staining with Phalloidin.

After transfection of CCD-1113sk cells with the siRNA, the cells were cultured for 1 day, and 5×10⁴ cells were then seeded in a 6-well plate containing submerged cover glasses. In this process, Human rTGF-β1 (100-B-010, R&D Systems) was added to a final concentration of 0 or 11 ng/mL, and the culture was carried out for 3 days. Thereafter, the cells were washed twice with PBS, and 10% neutral formalin was added thereto, followed by fixation for 20 minutes at room temperature. The cells were then washed twice with PBS, and then treated with PBS supplemented with 0.2% Triton-X100 for 15 minutes, followed by washing the cells 3 times with TBS. Thereafter, 5 unit/well of Phalloidin Alexa 488 (A-12379, Invitrogen) was added to the wells, and the treatment was carried out for 20 minutes at room temperature. The cells were washed 3 times with TBS, and the slide glass was then removed, followed by embedding the cells using Fluoromount (K024, Diagnostics BioSystems (Cosmo bio)) and observing the cells under a fluorescence microscope (ECLIPSE E600, Nikon). The results are shown in FIG. 3. The upper left panel shows the result obtained by the system with addition of the negative control siRNA in the presence of 11 ng/mL TGF-β, and the upper right panel shows the result obtained by the system with addition of the ETFB siRNA in the presence of 11 ng/mL TGF-β. The lower panels are enlarged views of the upper panels. From these results, it can be seen that formation of actin filaments is not found in the system with addition of the siRNA even in the presence of TGF-β.

Figure 4:
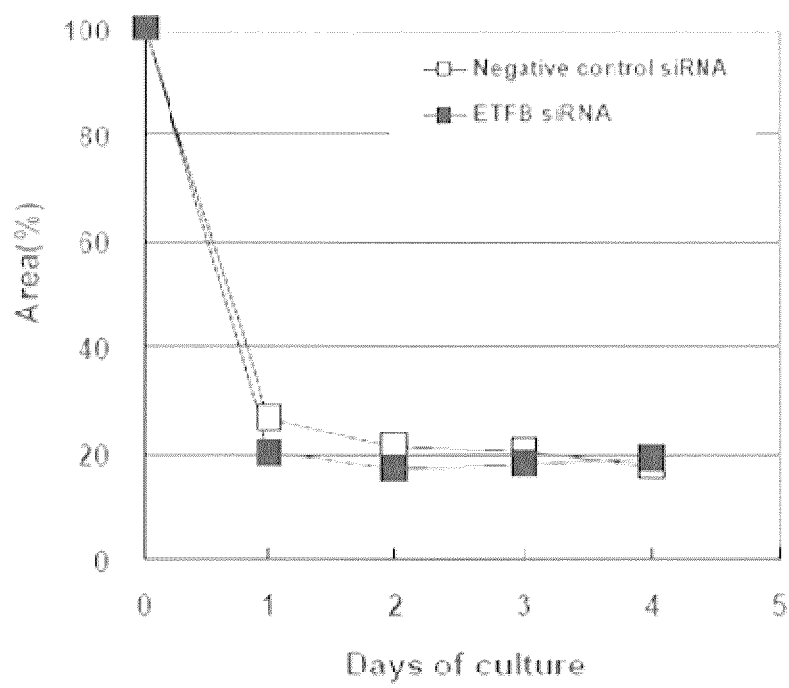
FIG. 4 is a diagram illustrating the influence of the ETFB siRNA of Example 1 on collagen gel contraction. After introduction of the ETFB siRNA or a negative control siRNA into cells, the cells were cultured in a collagen gel, and gel contraction was observed (n=6).

Whether or not the ETFB siRNA-transfected cells causes delay of gel contraction was investigated. As a result, the contraction rate observed with the ETFB siRNA-transfected cells was 20% on Day 1 of the culture, which was the same as the contraction rate observed with the fibroblasts treated with the negative control siRNA. The contraction rates observed thereafter were also not different from those of the negative control (see FIG. 4). Thus, it was suggested that loss of the function of ETFB does not adversely affect the action to close a wound. Further, this experiment result suggested that keloidal fibroblasts such as those of hypertrophic scars also show a behavior similar to that of normal fibroblasts. This means that the method of the present invention is also applicable to growth of fibroblasts in keloids and the like.

Excessive collagen expression is caused by differentiation of fibroblasts into myofibroblasts, and increased expression of SMA (α-smooth muscle actin) has been reported as a marker for differentiation of fibroblasts into myofibroblasts. The increased expression of SMA is caused by stimulation by TGF-β. If suppression of the function of ETFB suppresses expression of collagen and SMA, this factor may suppress hypertrophy by suppression of excessive growth of fibroblasts, and moreover, this factor may be hopeful as a therapeutic agent for hypertrophic scar. In view of this, behaviors of the above factors were observed.

Figure 5:
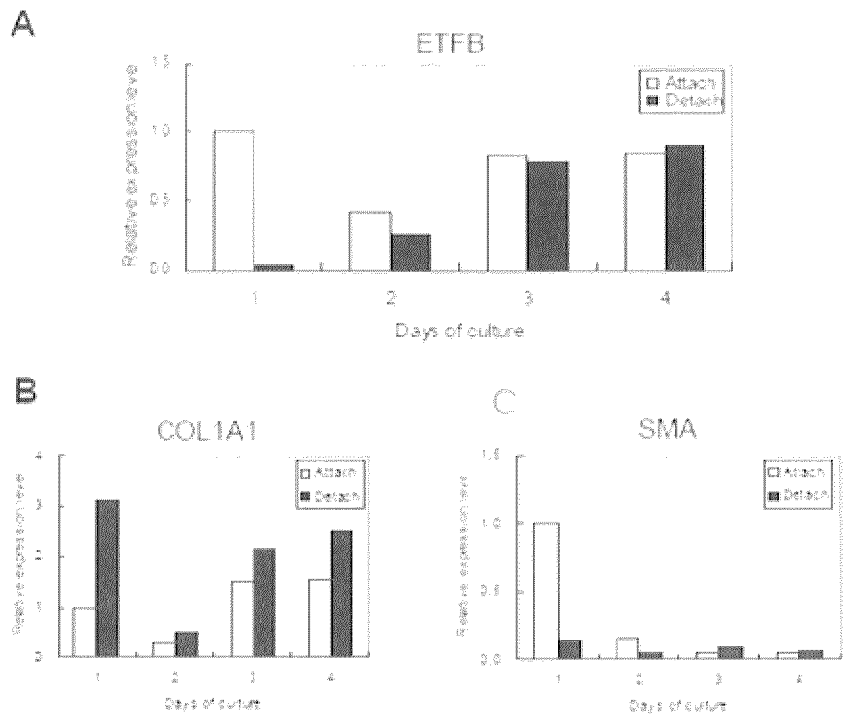
FIG. 5 is a diagram illustrating the influence of the ETFB siRNA of Example 1 on the amount of production of RNA encoding α-smooth muscle actin (SMA) (negative control). After introduction of the ETFB siRNA or a negative control siRNA into cells, the cells were cultured in a collagen gel while RNA was recovered daily during the culture to observe expression of mRNA of collagen 1A1 (COL1A1) (B) and SMA (C) by qRT-PCR. Panel A shows the expression level of ETFB in the attached state and detached state after the introduction of the negative control siRNA; Panel B shows the expression level of COL1A1 in the attached state and detached state after the introduction of the negative control siRNA; and Panel C shows the expression level of SMA in the attached state and detached state after the introduction of the negative control siRNA.

First, behaviors of ETFB, COL1A1 and SMA mRNAs during culture in a collagen gel in the attached state were investigated after transfection with the negative control or the ETFB siRNA (FIG. 5). In the negative control, the expression level of ETFB increased until Day 3 of the culture. The expression level of COL1A1 increased until Day 3 of the culture, although the expression level showed some fluctuation. The expression level of SMA was maximum on Day 1, and decreased thereafter. On the other hand, in the group treated with the ETFB siRNA, expression of ETFB was hardly observed until Day 4 of the culture, indicating that the effect of the siRNA was maintained.

Figure 6:
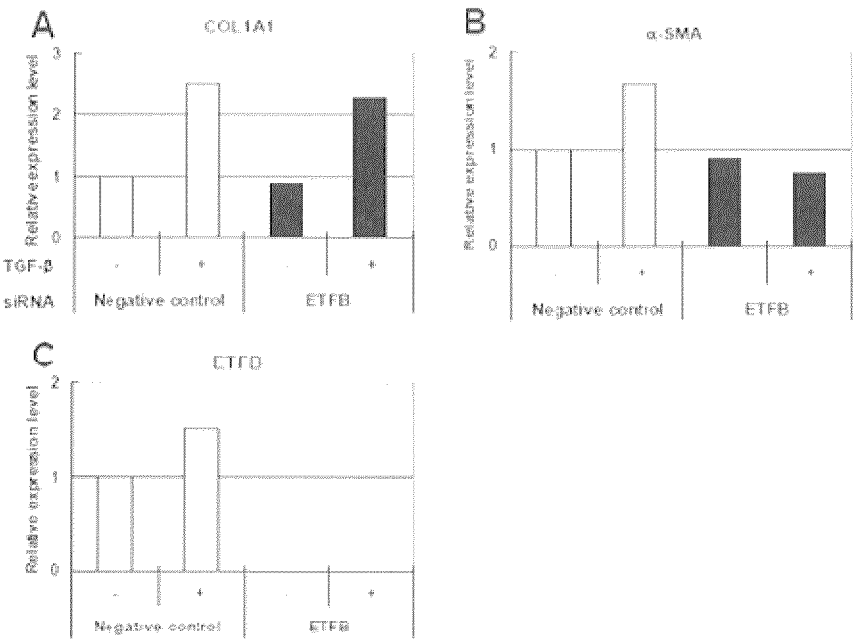
FIG. 6 is a diagram illustrating the influence of the ETFB siRNA of Example 1 on collagen production and SMA production. After introduction of the ETFB siRNA or a negative control siRNA into cells, the cells were cultured in a collagen gel that was supplemented with TGF-β (300 ng/ml) or not supplemented therewith, and RNA was recovered on Day 1 of the culture to observe expression of mRNAs of COL1A1(A), SMA(B) and ETFB(C) by qRT-PCR. Panel A shows changes in the expression level of COL1A1 in the presence or absence of TGF-β, or by introduction of the negative control siRNA or the ETFB siRNA; Panel B shows changes in the expression level of SMA in the presence or absence of TGF-β, or by introduction of the negative control siRNA or the ETFB siRNA; and Panel C shows changes in the expression level of ETFB in the presence or absence of TGF-β, or by introduction of the negative control siRNA or the ETFB siRNA.

The influence of loss of the function of ETFB on expression of collagen and SMA in culture in a collagen gel in the presence of TGF-β was investigated. CCD-1113sk cells were transfected with a negative control or the ETFB siRNA, and rTGF-β was added to a final concentration of 300 ng/mL to the collagen gel solution prepared upon starting the culture in a collagen gel. On Day 1 of the culture, the cells were recovered using collagenase, and the expression levels of ETFB, COL1A1 and SMA mRNAs were measured (FIG. 6). As a result, the expression level of ETFB increased about 1.5-fold by addition of TGF-β. The expression level of COL1A1 increased 2- to 2.5-fold by addition of TGF-β in both negative control treatment and ETFB siRNA treatment. On the other hand, the expression level of SMA increased 1.7-fold by addition of TGF-β in the negative control, while the ETFB siRNA-treated group did not show an increase in the expression level. From these results, it can be seen that loss of the function of ETFB suppresses growth of fibroblasts caused by tension but does not influence collagen expression, so that an increase in SMA expression, that is, differentiation into myofibroblasts, can be suppressed.

From these results, ETFB was demonstrated to be a factor for abnormal growth of fibroblasts. It can also be seen that, by monitoring changes in ETFB, the probability of occurrence of abnormal growth of fibroblasts such as formation of scars can be judged. Further, by judging changes in ETFB caused by test substances in the presence and absence of tension in culture of fibroblasts a collagen gel, components that suppress abnormal growth of fibroblasts can be screened. Further, a component suppressing abnormal growth of fibroblasts, screened under such conditions, enables not only suppression of growth of fibroblasts but also suppression of an increase in SMA expression, that is, differentiation into myofibroblasts. Thus, it can be seen that the component suppresses growth of fibroblasts and also suppresses excessive collagen expression caused by differentiation of fibroblasts into myofibroblasts, and therefore that the component can be used as a therapeutic and prophylactic agent for diseases in which such phenomena are involved, that is, fibrosis, hypertrophic scars and the like.

INDUSTRIAL APPLICABILITY

The present invention is applicable to development of pharmaceuticals for suppression of abnormal growth of fibroblasts.

The invention claimed is:

1. A method for identifying the pathogenic state of hypertrophic scar which is a fibrosis due to differentiation of fibroblasts into myofibroblasts using as an index the level of expression of ETFB (electron transfer flavoprotein beta subunit) in collected fibroblasts, comprising:

measuring the level of expression of ETFB in the fibroblasts of a test sample and the expression level in control fibroblasts, wherein said expression of ETFB is RNA expression measured by polymerization chain reaction with primers which are the oligonucleotide of SEQ ID NO: 1 and the oligonucleotide of SEQ ID NO: 2, comparing the level of expression of ETFB of the test sample with the expression level in control fibroblasts, determining that hypertrophic scar formation is promoted in cases where the level of expression of ETFB of the test sample is higher than the expression level in control fibroblasts, and determining that hypertrophic scar formation is suppressed in cases where the level of expression of ETFB is the same as or lower than the expression level in control fibroblasts.

2. A method for identifying the pathogenic state of hypertrophic scar which is a fibrosis due to differentiation of fibroblasts into myofibroblasts in an organ suspected of having fibrosis, using as an index the level of expression of ETFB in fibroblasts collected from the organ, comprising:

measuring the level of expression of ETFB in the fibroblasts of a test sample and the expression level in control fibroblasts, wherein said expression of ETFB is RNA expression measured by polymerization chain reaction with primers which are the oligonucleotide of SEQ ID NO: 1 and the oligonucleotide of SEQ ID NO: 2, comparing the level of expression of ETFB of the test sample with the expression level in control fibroblasts, determining that there is a high probability that the organ has hypertrophic scar formation in cases where the level of expression of ETFB of the test sample is higher than the expression level in control fibroblasts; and determining that there is only a low probability that the organ has hypertrophic scar formation in cases where no rise in ETFB of the test sample is found compared to the expression level in control fibroblasts.

3. The method for identifying the pathogenic state of hypertrophic scar according to claim 2, wherein said organ is skin.

4. A method for identifying the differentiation state of fibroblasts into myofibroblasts using as an index the level of expression of ETFB, comprising:

measuring the level of expression of ETFB in the fibroblasts of a test sample and the expression level in control fibroblasts, wherein said expression of ETFB is RNA expression measured by polymerization chain reaction with primers which are the oligonucleotide of SEQ ID NO: 1 and the oligonucleotide of SEQ ID NO: 2, comparing the level of expression of ETFB of the test sample with the expression level in control fibroblasts, determining that differentiation of fibroblasts into myofibroblasts is promoted in cases where the level of expression of ETFB of the test sample is higher than the expression level in control fibroblasts, and determining that differentiation of fibroblasts into myofibroblasts is normal in cases where the level of expression of ETFB is the same as or lower than the expression level in control fibroblasts.

5. A method for identifying a fibrosis-suppressing agent, comprising:

culturing fibroblasts under tension in a collagen gel in the presence and absence of a test substance; and judging the test substance to be a fibrosis-suppressing agent in cases where the expression level of ETFB is lower in the culture in the presence of the test substance than in the culture in the absence of the test substance, wherein said expression of ETFB is RNA expression measured by polymerization chain reaction with primers which are the oligonucleotide of SEQ ID NO: 1 and the oligonucleotide of SEQ ID NO: 2.

6. The method for identifying fibrosis-suppressing agent according to claim 5, wherein said fibrosis is hypertrophic scar formation.

7. The method for identifying a fibrosis-suppressing agent according to claim 6, wherein said fibrosis is a hypertrophic scar in skin.

* * * * *